United States Patent

Zdarsky

[11] Patent Number: 5,752,598
[45] Date of Patent: May 19, 1998

[54] DISPENSER FOR STORAGE OF MARKER DISKS USED IN ROOT CANAL THERAPY

[75] Inventor: Constantin Zdarsky, Palm Beach, Fla.

[73] Assignee: Vereinigte Dentalwerke Antaeos Beutelrock Zipperer Zdarsky Ehrler GmbH & Co. KG, Munich, Germany

[21] Appl. No.: 675,907

[22] Filed: Jul. 5, 1996

[30] Foreign Application Priority Data

May 31, 1996 [DE] Germany ............. 196 22 034.5

[51] Int. Cl.⁶ ............ A61B 19/02; B65D 83/04; B65D 85/00
[52] U.S. Cl. ............. 206/63.5; 206/369; 206/445; 206/469; 433/77
[58] Field of Search ............... 206/63.5, 369, 206/531, 532, 538, 445, 461, 468, 469, 467; 433/72, 77

[56] References Cited

U.S. PATENT DOCUMENTS

| | | | |
|---|---|---|---|
| 3,134,210 | 5/1964 | Dreyfus | 203/461 X |
| 3,358,826 | 12/1967 | Siegel | 206/368 |
| 3,382,972 | 5/1968 | Phipps | 206/468 |
| 3,809,221 | 5/1974 | Compere | 206/461 |
| 3,812,963 | 5/1974 | Zahuranec et al. | 206/468 |
| 3,856,144 | 12/1974 | Kelly | 206/469 X |
| 3,912,081 | 10/1975 | Haines et al. | 206/469 X |
| 4,988,004 | 1/1991 | Intini | 206/469 X |
| 5,154,611 | 10/1992 | Chen | 433/77 |
| 5,244,091 | 9/1993 | Tannenbaum | 206/469 X |
| 5,368,187 | 11/1994 | Poncetta et al. | 206/531 X |
| 5,486,390 | 1/1996 | Burns et al. | 206/531 X |

FOREIGN PATENT DOCUMENTS

34 19 712 C2  5/1984  Germany.

*Primary Examiner*—Bryon P. Gehman
*Attorney, Agent, or Firm*—Lowe, Price, LeBlanc & Becker

[57] ABSTRACT

A dispenser for marker disks to limit the depth of penetration of root-canal preparatory instruments is composed of a plastic base foil of such a strength that it may be punctured by a root-canal preparatory instrument. Deep-drawn recesses are formed in the base foil such that the marker disks are received on one of their large sides in the recesses in a plane running parallel to the base foil. A strip-off sheet is present above the base foil with which it is connected and in particular may be stripped off in segments from the base foil such that the recesses arrayed in rows or columns are uncovered. The root-canal preparatory instrument is able to puncture both the uncovered marker disk and the base foil below the recess until the marker disk has been mounted at the desired position on the root-canal preparatory instrument.

6 Claims, 3 Drawing Sheets

5,752,598

1

DISPENSER FOR STORAGE OF MARKER DISKS USED IN ROOT CANAL THERAPY

TECHNICAL FIELD

The invention concerns a dispenser for marker disks used in limiting the depth of penetration of dental root-canal preparatory instruments and the like.

BACKGROUND ART

Because root-canal preparatory instruments may penetrate the root canal only to a specified depth, marker disks for instance made of silicone are used as stops to mark the permissible depth of penetration to which drilling may take place. These marker disks are mounted on the root-canal preparatory instruments at the corresponding location.

German patent document 3,419,712 C2 describes a dispenser for such marker disks which is meant to facilitate the mounting of the these disks on a root-canal preparatory instrument. This known dispenser comprises a receiving chamber wherein the marker disks are held in arbitrary arrangements, said chamber communicating with a cavity of which the height substantially corresponds to the marker-disk thickness, as a result of which the marker disks may be selected to place them one at a time in a specific position at a dispenser aperture where they may be mounted in impaled manner on a root-canal preparatory instrument.

The object of the invention on the other hand is to create a dispenser of the initially cited species which evinces a simple design and will be accordingly economical and which in particular allows sterilizing the marker disks and to store them in sterile manner.

SUMMARY OF THE INVENTION

This problem is solved by the invention of a plastic base foil evincing proper strength to allow it being punctured by a by root-canal preparatory instrument, deep-drawn recesses being present in the base foil for the marker disks in such a manner that the marker disks are received to lie flat on one of their sides in a plane parallel to said base foil, and by a cover detachably connected to said base foil.

Accordingly a dispenser of the invention allows storing the marker disks in a defined position in their particular recesses and as a result the removal of the cover from the base foil lays open the marker disks which then can be pulled onto a root-canal preparatory instrument which pierces both a marker disk and the base foil at the particular recess until the marker disk has been pulled up to the desired position at the root-canal preparatory instrument.

Because the dispenser of the invention is in two parts, it can be manufactured simply and economically.

In particular when the cover is designed to uncover, solely in step-wise manner, the recesses filled with marker disks, for instance in rows or one at a time, then the remaining marker disks will reliably remain sterile.

2

DETAILED DESCRIPTION OF THE INVENTION

Figure 1:
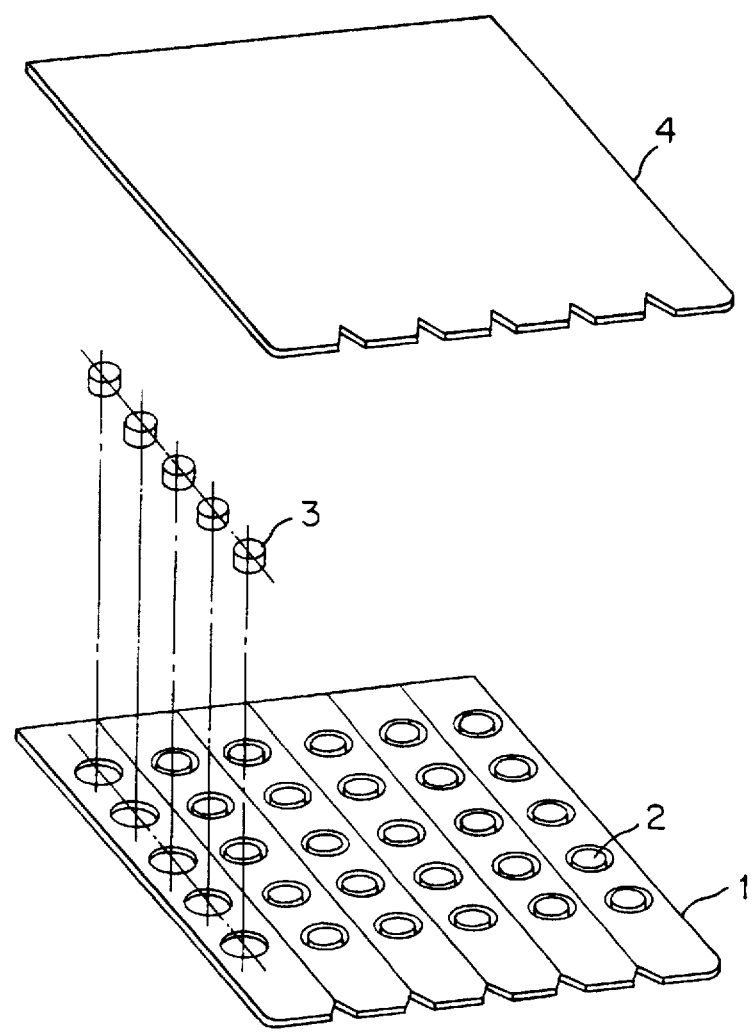
FIG. 1 is an exploded perspective view of the first embodiment.

The dispenser shown in FIG. 1 dispensing marker disks 3 to limit the depth of penetration of dental root-canal preparatory instruments comprises a base foil 1 which is made of a plastic such as polystyrene and which can be punctured by a root-canal preparatory instrument the foil comprises deep-drawn recesses 2 which are designed to receive the marker disks lying on their large surface in them. Accordingly the marker disks 3 lie flat in a plane running parallel to the plane of the base foil 1.

In the embodiment of FIG. 1, a cover in the form of a strip-off sheet 4 is mounted above the assembly of the base foil 1 with the marker disks 3 lying in the recesses 2. Illustratively the strip-off sheet 4 is made of aluminum fitted with a thin sealing layer and is bonded under pressure and heat to the base foil 1.

As also shown in FIG. 1, the recesses 2 for the marker disks 3 are arrayed in parallel rows or columns. If the strip-off sheet 4 is fitted with tear-off lines as shown in FIG. 2, where said lines run between the rows or columns of recesses 2, then by tearing open the strip-off sheet 4 only along one row or column it is possible to remove the marker disks 3 singly without uncovering the remaining marker disks 3 in their recesses 2, these remaining disks are therefore kept sterile in their recesses 2.

Figure 2:
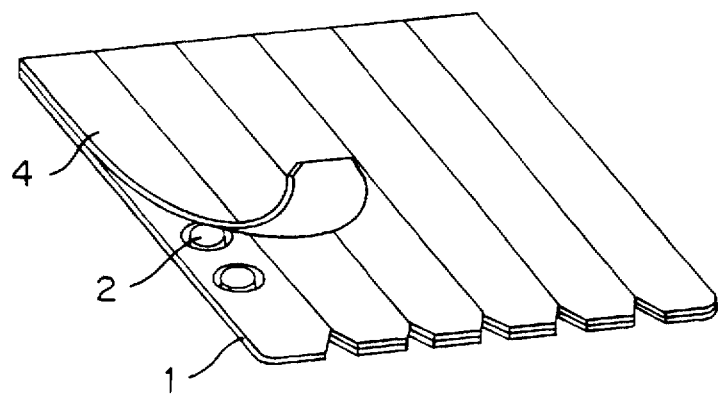
FIG. 2 is a perspective of embodiment shown in FIG. 1 when a marker disk is being removed.

As shown in FIG. 2, this feature is facilitated by making the base foil 1 and/or the strip-off sheet 4 is tab-shaped at one edge of the dispenser.

When manufacturing such a dispenser, first the base foil 1 is deep-drawn and fitted with the recesses 2, and then the marker disks 3 are placed into the recesses 2, where called for concurrently with a sterilization procedure, and thereupon the strip-off sheet 4 is deposited and sealed.

Figure 3:
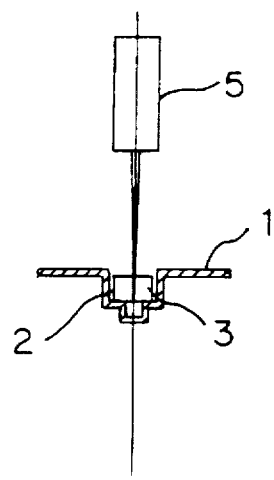
FIG. 3 is a cross-section of a recess together with marker disks, the marker disk is being pulled up on a root-canal preparatory instrument.

In operation, the strip-off sheet 4 is torn open along a row or column as shown in FIG. 2 until at least one recess 2 with the marker disk 3 contained therein has been uncovered. As shown in FIG. 3, because of the defined position of the marker disk 3, this maker disk 3 and the base foil 1 can be punctured at the bottom of the recess 2 by a root-canal preparatory instrument 5 and thereby the marker disk 3 can be pulled up on the said root-canal preparator instrument as far as the desired location.

When using a dispenser of the above design, the defined position of the marker disk 3 in the recess 2 assures that the root-canal preparatory instrument 5 shall puncture the right sites, and because of this possibility the procedure can be carried out in a sterile manner without touching the marker disk by hand.

Figure 4:
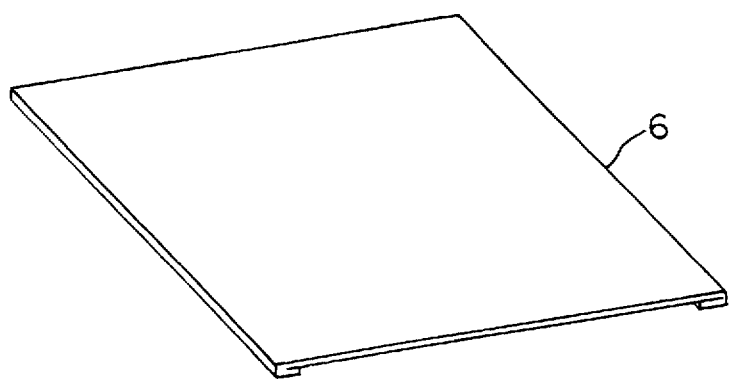
FIG. 4 is a perspective view of the cover for a second embodiment.

FIG. 4 shows the cover in a further embodiment. In this latter embodiment, the cover is in the form of a slider 6 which after the recesses 2 of the base foil have been filled with marker disks 3 will be pushed over the base foil. By sliding the slider 6 relative to the base foil 1, the recesses 2 together with the marker disks 3 therein can be uncovered by rows or columns and as a result individual marker disks 3 may be picked up by a root-canal preparatory instrument. Only one row of marker disks 3 is uncovered at a time, the other marker disks 3 remaining covered.

I claim:

1. A marker-disk dispenser, comprising:

a plurality of marker disks individually usable and structured to limit a depth of penetration of a dental root canal preparatory instrument;

a plastic base foil puncturable by said root canal preparatory instrument, said base foil including a plurality of recesses respectively receiving said marker disks in a plane parallel to the base foil; and a cover detachably connected to the base foil.

2. A dispenser as defined in claim 1, wherein said cover is a strip-off sheet (4).

3. A dispenser as defined in claim 2, wherein the recesses in the base foil (1) are arrayed in mutually parallel rows or columns and the strip-off sheet (4) is fitted with mutually parallel tear-off lines running between the rows or columns of the recesses (2).

4. A dispenser as defined in claim 1, wherein the cover is a slider (6) displaceable relative to the base foil (1).

5. A marker disk dispenser according to claim 1, wherein said disks are cylindrical and have opposing circular faces defining a diameter greater than a thickness between said faces.

6. A marker disk dispenser according to claim 5, wherein said disks are individually laid flat in said recesses, said recesses being of corresponding cylindrical shape.

* * * * *